United States Patent [19]

Tan et al.

[11] Patent Number: 5,668,262
[45] Date of Patent: Sep. 16, 1997

US005668262A

[54] METHOD OF TRITIUM LABELING OLIGONUCLEOTIDES

[76] Inventors: Weitian Tan, 1612 Worcester Rd., Framingham, Mass. 01701; Radhakrishnan P. Iyer, 34 I Shrewsbury Green Dr., Shrewsbury, Mass. 01545; Zhiwei Jiang, 1 Brian Cir., Grafton, Mass. 01519; Dong Yu, 25 Yorkshire Ter. Apartment 9, Shrewsbury, Mass. 01545; Sudhir Agrawal, 61 Lamplighter Dr., Shrewsbury, Mass. 01545

[21] Appl. No.: 485,112

[22] Filed: Jun. 7, 1995

Related U.S. Application Data

[62] Division of Ser. No. 447,203, May 22, 1995.

[51] Int. Cl.$^6$ .................... C07H 19/00; C07H 21/00; C07H 21/02; C07H 21/04
[52] U.S. Cl. ........................ 536/22.1; 536/25.3
[58] Field of Search ................ 536/22.1, 25.3, 536/25.32

[56] References Cited

U.S. PATENT DOCUMENTS 4,521,592 6/1985 Dahmen et al. .................... 536/4.1

OTHER PUBLICATIONS

Bayever et al., *Antisense Res. and Dev.* 3, 383 (1993).
Garegg et al., *Chemica Scripta* 25, 280–282 (1985).
Sasmor et al., *J. Labeled Compd. and Radiopharm.* 36, 15–31 (1995).
Onodera et al., *Carbohydrate Research* 6, 276 (1968).
Parikh and von E. Doehring, *J. Am. Chem. Soc.* 89, 5505 (1967).
Dess and Martin, *J. Org. Chem.* 48, 4155 (1983).
House, *Modern Synthetic Reactions*, Chapter 2, pp. 23–49 (W.A. Benjamin Inc., New York. 1965).
March, *Advanced Organic Chemistry: Reactions and Mechanisms*, pp. 809–814 (Third Ed., John Wiley & Sons. 1985).

Agrawal, *TIBTECH* 10, 152–158 (1992).
Stein and Cheng, *Science* 261, 1004 (1993).
Agrawal and Tang, *Antisense Res. and Dev.* 2, 261 (1992).
Agrawal et al., *Clin. Pharmacokinet.* 28, 7–16 (1995).
Southern, *J. Mol. Biol.* 98, 503–517 (1975).
Sambrook et al., *Molecular Cloning: A Laboratory Manual*, 2nd Ed., Cold Spring Harbor Laboratory Press (1989).
Agrawal et al., *Natl. Acad. Sci. USA* 88, 7595–7599 (1991).
Beaucage and Caruthers, *Tetrahedron Lett.* 22, 1859–1862 (1981).
Graham et al., *Nucleic Acics Res.* 21, 3737–3743 (1993).
Pfitzner and Moffatt, *J. Am. Chem. Soc.* 87, 5661–5770 (1965).
Jones and Moffatt, in *Methods in Carbohydrate Chemistry*, vol. 6, pp. 315–322 (1972).
Albright and Goldman, *J. Am. Chem. Soc.* 87, 4214 (1965).
Berger et al., *Nucleosides and Nucleotides* 6, 395–396 (1987).
Dess and Martin, *J. Am. Chem. Soc.* 113, 7277–7287 (1991).

*Primary Examiner*—W. Gary Jones
*Assistant Examiner*—Ethan Whisenant
*Attorney, Agent, or Firm*—Michael S. Greenfield; McDonnell Boehnen Hulbert & Berghoff

[57] ABSTRACT

The present invention comprises a novel method of incorporating a tritium label at one or more predetermined sites within an oligonucleotide. In particular, the method comprises contacting a nascent, support-bound oligonucleotide having a free 5' hydroxyl group with a suitable oxidizing agent to oxidize the alcohol to an aldehyde, followed by reducing the aldehyde thereby formed with a suitable tritium labeled reducing agent such as [$^3$H]NaBH$_4$ to yield the 5' terminal alcohol with a 5' tritium label. Normal automated synthesis can then be continued to yield the oligonucleotide of desired length having the tritium label in the desired location. The oligonucleotides thereby produced have higher specific activity than those previously known in the art. According, in a second aspect, the present invention provides oligonucleotides having high specific activity. The oligonucleotides of the present invention are useful for determining the pharmacokinetics and biodistribution of their non-radiolabeled counterparts, both in vitro and in vivo.

8 Claims, 3 Drawing Sheets

METHOD OF TRITIUM LABELING OLIGONUCLEOTIDES

This application is a division of U.S. Application Ser. No. 08/447,403, filed May 22, 1995.

BACKGROUND OF THE INVENTION

1. Field of the Invention

This invention relates to synthetic methods of site-specifically radiolabeling oligonucleotides with $^3$H.

2. Summary of the Related Art

Recently, considerable interest has been generated in the development of synthetic oligonucleotides as therapeutic or gene expression modulating agents in the so-called antisense approach. For example, Agrawal, *Trends in Biotechnology* 10, 152–158 (1991) extensively reviews the development of antisense therapeutic approaches. Oligonucleotide phosphorothioates (PS-oligos) have shown great therapeutic potential as antisense-mediated inhibitors of gene expression (Stein and Cheng, *Science* 261, 1004 (1993) and references therein) as evidenced by a number of ongoing clinical trials against AIDS and cancer. Agrawal and Tang, *Antisense Res. and Dev.* 2, 261 (1992) and references therein; and Bayever et al., *Antisense Res. Dev.* 3, 383 (1993).

For an antisense therapeutic approach to be effective, oligonucleotides must be introduced into a patient and must reach the specific tissues to be treated. The biodistribution and pharmacokinetics of a therapeutic drug must be determined as a step preliminary to treatment with the drug. Consequently, there is a need to be able to detect oligonucleotides in body fluids or tissues. Agrawal et al., *Clin. Pharmacokinetics* 28, 7 (1995), reviews certain aspects of the pharmacokinetics of antisense oligonucleotides.

Detection of specific nucleic acid sequences present in cells is generally known in the art. Southern, *J. Mol. Biol.* 98, 503–517 (1975) teaches detection of specific sequences among DNA fragments separated by gel electrophoresis using "blotting" or transfer of the DNA fragments to a membrane followed by hybridization of denatured DNA fragments with a radioactive probe and autoradiography. This procedure has also been extended to the detection of RNA molecules extracted from cells or tissues. E.g., Sambrook et al., *Molecular Cloning: A Laboratory Manual* pp. 7.37–7.52 (Cold Spring Harbor Laboratory Press, 2d Ed. 1989). More recently, faster and quantitative "dot-blotting" procedures have been developed for rapid detection of DNA or RNA from tissues or cells. U.S. patent application Ser. No. 08/368,243 discloses method for detecting the presence of unlabeled synthetic oligonucleotides in body fluids or tissue samples taken from laboratory animal and human patients. In that method, body fluid or tissue samples are taken from an animal or human to whom an oligonucleotide has been altered and are proteolytically digested, then extracted. Total nucleic acids are then transferred to a hybridization membrane. The hybridization membrane with attached nucleic acids is prehybridized, then hybridized with a labeled oligonucleotide that is complementary to the oligonucleotide that was administered to the animal or patient. Presence of hybridized, labeled oligonucleotide is then detected by standard procedures.

Another well-established approach used in in vivo pharmacokinetic studies of pharmacological compounds such as antisense oligonucleotides entails radiolabeling the compounds to enable detection. In animal models, radiolabeled oligonucleotides have been administered to the animal and their distribution within body fluids and tissues has been assessed by extraction of the oligonucleotides followed by autoradiography (See Agrawal et al., *Proc. Natl. Acad. Sci.* 88, 7595–7599 (1991).

$^{35}$S-labeling is an established and wide-spread technique. For biological studies, $^{35}$S-labeled oligonucleotide phosphorothioates have been prepared using H-phosphonate chemistry. Garegg et al., *Chem. Scr.* 25, 280–282 (1985).

Radioisotopic labeling of synthetic oligonucleotides with $^{14}$C and $^3$H is currently accomplished by using the well-established solid-phase automated synthesis. Beaucage and Caruthers, *Tetrahedron Lett.* 22, 1859–1862 (1981). In this approach, the assembly of $^{14}$C or $^3$H nucleoside phosphoramidite (3) requires a two-step process (FIG. 1). Sasmor et al., *J. Labeled Compd. and Radiopharm.* 36, 15–31 (1995).

Several disadvantages are associated with this method: (a) since the radioisotope is introduced in the very first step, the radiochemical yield after two steps is limited; (b) this operation often suffers a dilution problem, namely, the natural abundance isotope is usually blended in as a carrier in order to maintain a manageable synthetic scale, resulting in lower specific activity of the final oligos; (c) the phosphoramidite 3 is a reactive species prone to degradation; choosing 3 as the final radioactive precursor leads to stringent storage and transportation requirements to prevent degradation, and the degraded products from 3 could cause insufficient coupling when in use; (d) it is difficult to recover [$^3$H]- or [$^{14}$C]-3 intact after the coupling reaction. This is costly considering that in the current coupling protocol 3 and tetrazole are used at more than 10 times excess. Sasmor et al., supra.

Other methods of radiolabeling oligonucleotides, while avoiding the dilution problem, lead to indiscriminate labeling in multiple positions. E.g., Graham et al., *Nucl. Acids Res.* 21, 3737 (1993) and references cited therein. Still other methods employ radiolabeling at exchangeable positions, which magnifies the dilution problem. Graham et al., supra.

In view of the deficiencies in the prior art, improved methods of radiolabeling oligonucleotides are desirable.

SUMMARY OF THE INVENTION

The present invention provides new methods for radiolabeling oligonucleotides. In particular, the present invention comprises methods for incorporating a $^3$H-label at the 5' position of one or more predetermined nucleosides within an oligonucleotide.

The present invention comprises a method of synthesizing oligonucleotides having $^3$H labels at one or more predetermined nucleoside 5' positions. The method comprises oxidizing the 5'-most hydroxyl group of a nascent oligonucleotide to yield a 5' aldehyde and reducing the 5' aldehyde with a tritiated reducing agent to yield the corresponding 5' primary alcohol bearing a $^3$H label on the 5' carbon. In a preferred embodiment of the invention, the alcohol is oxidized to the aldehyde with Moffatt-Pfitzner reagents, Dess-Martin periodinane, or DMSO/Ac$_2$O, and the resulting 5' aldehyde is treated with [$^3$H]NaBH$_4$ to yield the 5' $^3$H-labeled alcohol. FIG. 2.

The present method is particularly advantageous because it is conducted in situ. That is, the tritium label is added at the 5' position of the 5' most nucleotide of a nascent nucleotide chain that is attached to a solid support. The present method avoids the need to synthesize, isolate, and purify radiolabeled mononucleotides. Furthermore, the present method avoids the inevitable dilution process in which radioactive precursors are mixed with their natural abundance isotopes to maintain manageable synthetic scale.

Consequently, oligonucleotides synthesized according to the present method have high specific activity. In addition, the present method provides for oligonucleotides in which the tritium label is non-exchangeable, thereby avoiding indiscriminate labeling at multiple positions.

Oligonucleotides synthesized according to the present method are useful not only for determining the biodistribution of their unlabeled counterparts, but also for determining biostability. Thus, oligonucleotides of the invention are useful to study the pharmacokinetics of therapeutic oligonucleotides in vivo. These oligonucleotides are particularly well-suited for pharmacokinetics studies because the $^3$H label is long-lived (having a half-life of 12 years) and nonexchangeable. Tritium-labeled oligonucleotides are also useful for studying the mechanism of oligonucleotide biodegradation as well as studying products of such degradation. Furthermore, the radiolabelled oligonucleotides of the invention can be used as probes in conventional hybridization assays.

The present invention also provides tritium-labeled oligonucleotides having higher specific activity than has previously been possible to obtain. The specific activity of the $^3$H-labeled oligonucleotides obtained from prior art techniques (which use $^3$H-labeled mononucleoside synthons) is limited by the specific activity of the $^3$H-labeled mononucleoside synthons used in the synthesis. In practice, the upper limit of the specific activity of $^3$H-labeled oliognucleotides of the prior an has been about 60 µCi/µmol. Because the present method uses redox chemistry in which the tritiated reducing agent (e.g., [$^3$H]NaBH$_4$) can be readily obtained with much higher specific activities than tritium labeled mononucleoside synthons, oligonucleotides according to the invention have specific activities from between about 200 µCi/µmol to about 1.5 mCi/µmol.

The foregoing merely summarizes certain aspects of the invention and is not intended, nor should it be construed, to limit the invention in any manner. All patents and other documents cited in this specification establish the state of the an and are hereby incorporated by reference in there entirety.

DETAILED DESCRIPTION OF THE PREFERRED EMBODIMENTS

Because of the ever-increasing interest in antisense oligonucleotides as therapeutic agents, there is a need to determine the pharmacokinetics properties of these compounds. It is also necessary to determine biodistribution as well as the half-lives and degradation products of antisense oligonucleotides intended for therapeutic use. One method of accomplishing these tasks is to label the oligonucleotides with $^3$H, a common isotopic label that allows for tracing and detecting biological compounds, both in vitro and in vivo. Tritium-labeled oligonucleotides are particularly well suited for these tasks when they are labeled as specific, predetermined sites.

In one aspect, the present invention comprises methods of synthesizing oligonucleotides having from one to all 5' $^3$H-labeled nucleotides. The locus or loci of the 5' tritium labels within the oligonucleotide are independent of each other and may be predetermined to be at any position.

Figure 2:
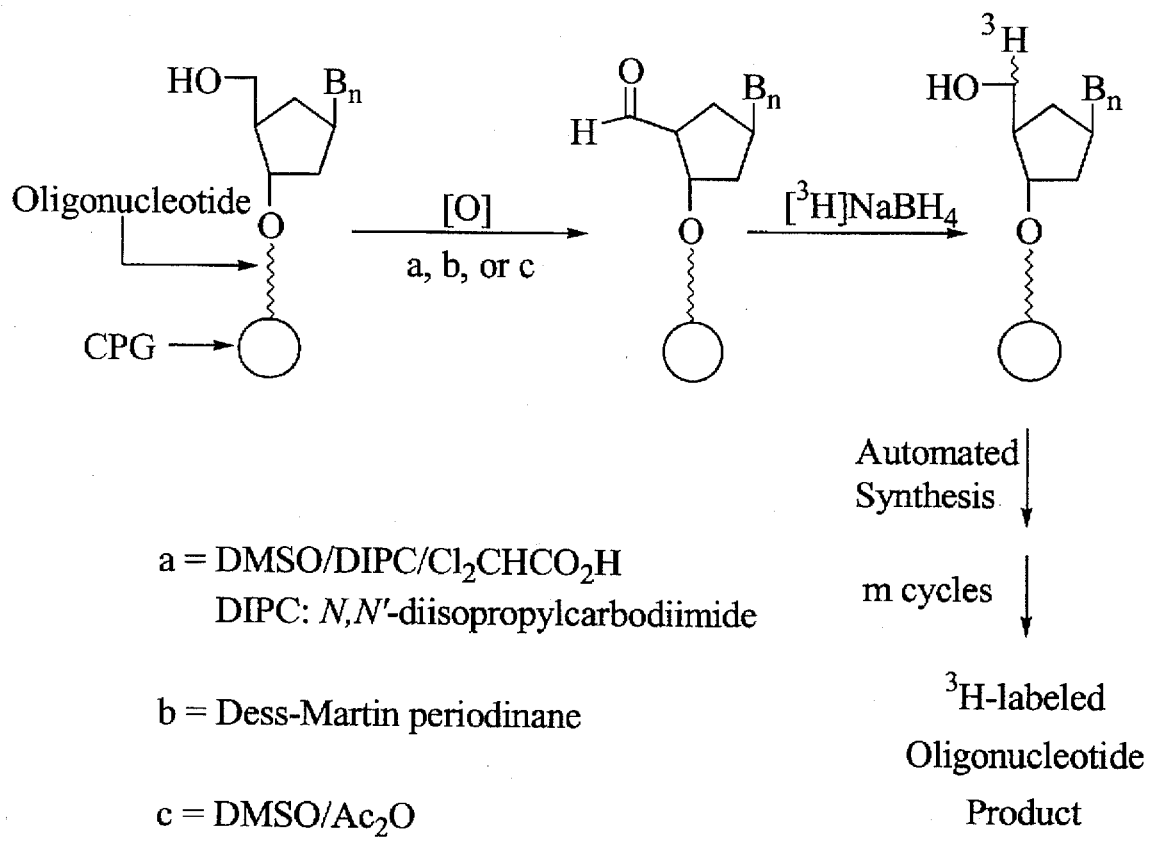
FIG. 2 is a schematic representation of tritium labeling oligonucleotides using the method of the invention.

The present method comprises contacting a nascent oligonucleotide with an oxidizing agent that will oxidize the 5'-most 5'-hydroxyl to an aldehyde and then contacting the aldehyde with a tritiated reducing agent, such as [$^3$H] NaBH$_4$. The entire method is conducted in situ and is depicted in FIG. 2. As used herein, the term "nascent oligonucleotide" means a nucleotide chain comprising one or more nucleotides anchored to a solid support.

The choice of the methods for the redox chemistry is dictated by the principle that minimal side reactions should occur on the functional groups of the oligonucleotides. That is to say, the redox process of the present invention operates in a neutral to slightly acidic condition to avoid any premature removal of the cyanoethyl group (used in phosphoramidite approach to oligonucleotide synthesis) or base protected groups, and to prevent premature hydrolysis of the succinyl ester linkage between the oligonucleotide and the solid support.

Any suitable oxidizing agent can be used to oxidize the 5'-most 5'-hydroxyl. In a preferred embodiment, the oxidizing agent is activated DMSO or a periodinane. In a particularly preferred embodiment, the oxidizing agent is (a) dimethylsulfoxide, N,N'-diisopropylcarbodiimide and dichloroacetic acid, (b) Dess-Martin periodinane, or (c) dimethylsulfoxide and acetic anhydride.

The use of activated DMSO as an oxidizing agent has been described. Moffatt and Pfitzner, *J. Am. Chem. Soc.* 87, 5661 (1965); Jones and Moffatt in *Methods in Carbohydrate Chemistry* vol. 6, pp. 315–322 (Whistler and BeMiller, Eds., Academic Press, New York 1972)); and Berger et al., *Nucleosides Nucleotides* 6, 395 (1987)). This method of oxidation involves the activation of DMSO with a suitable activating agent. The activating agents acetic anhydride (Albright and Goldman, *J. Am. Chem. Soc.* 89, 2416 (1967)), phosphorus pentaoxide (Onodera et al., *Carbohydrate Res.* 6, 276 (1968)), and a sulfur trioxide\pyridine complex (Parikh and von E. Doering, *J. Am. Chem. Soc.* 89, 5505 (1967)) have been described. Carbodiimide activating agents are preferred. Jones and Moffat, supra, Pfitzner and Moffatt, supra, and Berger et al., supra, all described the use of N,N"-dicyclohexyl carbodiimide (DCC). In a particularly preferred embodiment, N,N"-diisopropylcarbodiimide is used.

In this preferred embodiment of the method according to the invention, the alcohol (in the present case the nascent oligonucleotide with a free 5 hydroxyl) is contacted with three molar equivalents of a suitable carbodiimide and 0.5 molar equivalents of an appropriate acid in an appropriate solvent such as DMSO or a mixture of DMSO and an inert solvent. Other suitable solvents may be used, e.g., dimethylformaide. Suitable acids are those of intermediate strength (having a pKa of about 1.0 to about 3.5), such as anhydrous phosphoric acid, acetic acid, and dichloroacetic acid. Dichloroacetic acid is a preferred acid for use in the present invention.

Periodinanes are an alternative oxidizing agent useful for the facile and efficient oxidation of primary alcohols to aldehydes. Dess and Martin, *J. Am. Chem. Soc.* 113, 7277 (1991) (and references cited therein); and Dess and Martin, *J. Org. Chem.* 48, 4155 (1983). Particularly preferred is the so-called Dess-Martin periodinane, which has the structure:

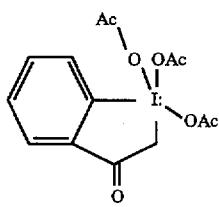

Quantitative conversion of the alcohol to the aldehyde is observed when a 5–10% molar excess of the Dess-Martin periodinane is used. Oxidation comprises dissolving the Dess-Martin periodinane reagent in an appropriate anhydrous solvent (e.g., chloroform, methylene chloride, and acetonitrile) and adding it to the nascent oligonucleotide having a free 5' hydroxyl group. The reaction proceeds under neutral and mildly acidic conditions and is complete within 2 hours at 25° C. The Dess-Martin reagent selectively oxidizes alcohols in the presence of non-hydroxylic functional groups such as sulfides, enol ethers, furans, and secondary amides.

In yet another embodiment, the oxidizing agent is DMSO in acid anhydrides. Albright and Goldman, *J. Am. Chem. Soc.* 87, 4214 (1965). Acetic anhydride is particularly preferred. An excess of DMSO and acetic anhydride is contacted with the nascent oligonucleotide having a free 5' hydroxyl and allowed to react at room temperature. The reaction is complete within 24 hours.

The oxidized nascent oligonucleotide is subsequently contacted with a suitable tritium hydride reducing agent, such as sodium borohydride, trifluoroacetoxyborohydride, alkoxyborohydride, and diisobutylaluminumhydride. In a preferred embodiment, about 40–65 mCi/μmol [$^3$H]NaBH$_4$ is used. The borohydride ion is a well known reducing agent. House, *Modern Synthetic Reactions*, ch. 2, pp. 23–49 (W. A. Benjamin Inc., N.Y. 1965); and March, *Advanced Organic Chemistry*, pp. 809–814 (Third Ed., John Wiley & Sons, New York 1985). The reaction is carried out at 25° C. in Tris-HCl buffer (pH 7.0, 30 min.). Other suitable buffers include 1M HEPES (pH 7.5) and 1M pyridinium trifluoroacetate (pH 5.0). This results in reduction of the 5' aldehyde to a primary alcohol with concomitant transfer of the tritium from the sodium borohydride to the 5' position of the nascent oligonucleotide. Additional nucleotides can then be added to the 5' end of the reduced nascent oligonucleotide bearing the 5' tritium label in the usual manner. The method of the present invention can be repeated at any step along the way and can be conducted to synthesize oligonucleotides with any modified or unmodified base and with any type of internucleotide linkage.

As the ordinary artisan will appreciate from the foregoing, the present method can be advantageously used synthesize oligonucleotides having one or more nucleosides 5'-labeled with any hydrogen isotope by using the appropriate reducing agent, such as sodium borodeuteride.

Figure 1:
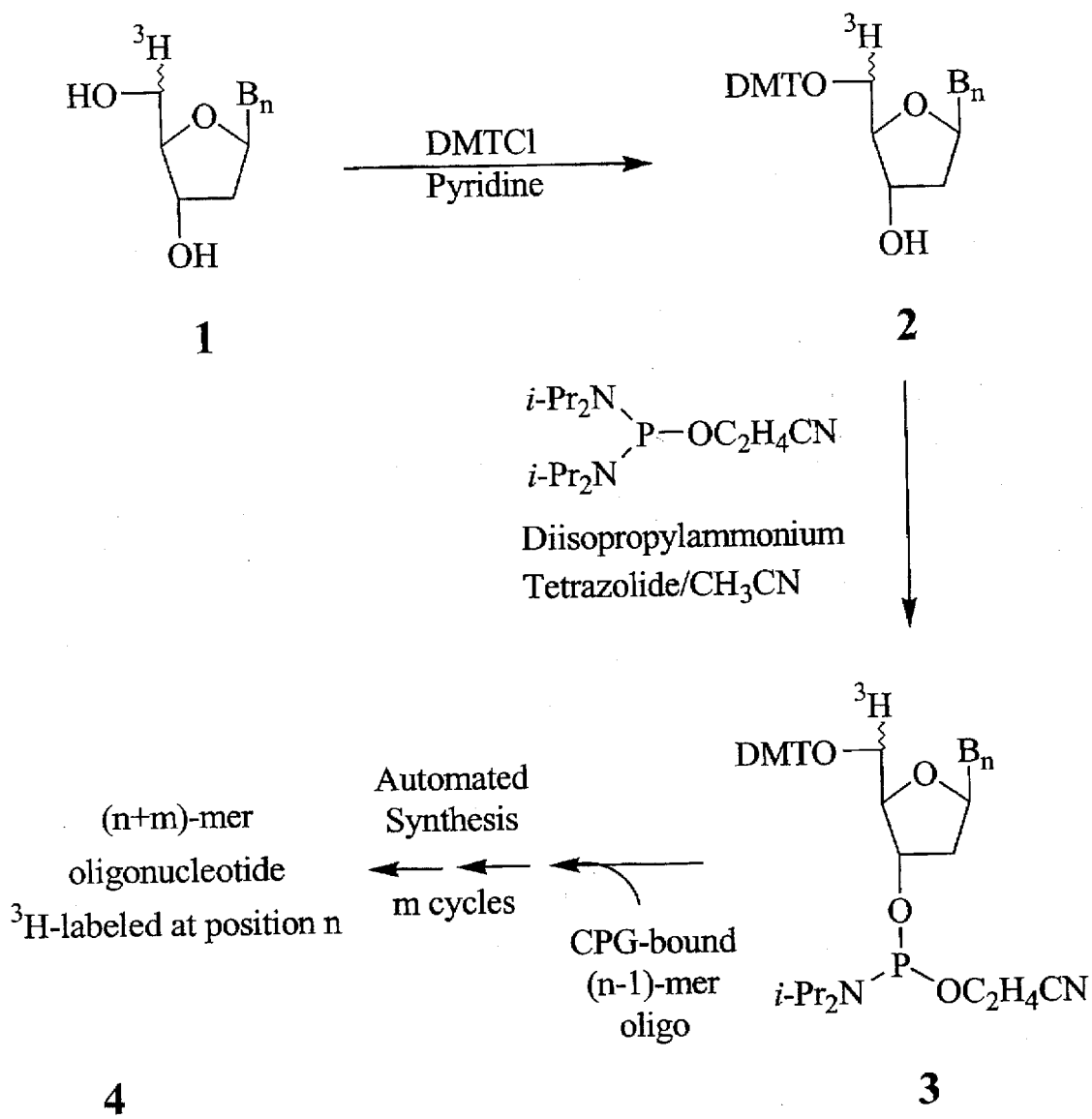
FIG. 1 is a schematic representation of the conventional approach of tritium labeling oligonucleotides.

By comparing FIG. 1 and FIG. 2, some advantages of the present invention are readily appreciated. In situ labeling results in higher yields of radiolabeled oligonucleotide because it avoids presynthesis of $^3$H-labeled nucleoside phosphoramidite monomers. Thus, the present method circumvents the need to isolate and purify the radioactive intermediate compounds 1–3 displayed in FIG. 1.

Furthermore, oligonucleotides with very high specific activity are more easily obtained using the present method, because the method eliminates the inevitable dilution process in which radioactive precursors are mixed with their natural abundance isotopes in order to maintain a manageable synthetic scale. The specific activity of oligonucleotides synthesized according to the invention can be adjusted downward, of course, by mixing in desired amounts of the non-radiolabeled counterpart.

The present invention further provides a method for synthesizing oligonucleotides with high specific activity having tritium labels at one or more predetermined sites. Furthermore, the tritium labels introduced by the present method are non-exchangeable, making the resulting oligonucleotides ideal for determining in vivo biological action.

Prior art techniques rely upon $^3$H-labeled mononucleoside synthons for the synthesis of $^3$H-labeled oligonucleotides, and the specific activity of the labeled oligonucleotides thereby produced is limited to that of the available labeled mononucleotide synthons, less the loss resulting from less than complete reaction. Typically, the upper limit of the specific activity of tritium labeled oligonucleotides synthesized by prior art techniques has been about 60 μCi/μmol. Because the methods of the present invention use a tritiated reducing agent with a specific activity many times greater than that of available $^3$H-labeled mononucleosides, the oligonucleotides of the present invention have a greater specific activity than has heretofor been possible. Furthermore, as noted before, the specific activity of the oligonucleotides can be adjusted downward by using a mixture of tritiated and untritiated reducing agent.

Accordingly, in another aspect of the invention, tritium-labeled oligonucleotides having from one to all 5'-tritium-labeled nucleosides and a specific activity of from about 100 μCi/μmol to about 1.5 mCi/μmol are provided. In a preferred embodiment, the specific activity of oligonucleotides according to the invention is about 200 μCi/μmol to about 1.2 mCi/μmol. In a particularly preferred embodiment, oligonucleotides according to this aspect of the present invention have specific activity of about 1.2 mCi/μmol.

The oligonucleotides synthesized by the method of the invention are particularly useful for determining biodistribution and pharmacokinetics of their non-radiolabeled oligonucleotide counterparts. Such methods are well known to those skilled in the art. E.g., Agrawal et al., *Clin. Pharmacokinetics*, supra.

Generally, however, oligonucleotides of the invention are useful for any purpose for which their non-radiolabeled oligonucleotide counterparts are useful. For example, oligonucleotides of the invention are valuable for studying the role of a targeted gene in biological processes, because the oligonucleotides are useful tools for easily and selectively inhibiting expression the targeted nucleic acid. The oligonucleotides of the present invention provide an alternative to the laborious method of gene mutation to inhibit expression and study the effect of loss of such expression. The importance of such an alternative is easily appreciated when one realizes that the elucidation of most known biochemical processes was determined by deletion mutation.

The following Examples are offered from illustrative purposes only and are not intended, nor should they be construed, to limit the invention in any manner

EXAMPLES

Example 1

Synthesis of $T^{2*}TT$

Using trithymidine nucleotide synthesis as a working model, we first synthesized a trityl-off TT dimer at 10 μmol scale on a CPG support followed by oxidation with a range of neutral or slightly acidic oxidants. Oxidation with DMSO/DIPC/Cl$_2$CHCO$_2$H, Dess-Martin periodinane, and DMSO/Ac$_2$O each gave the corresponding dithymidine 5'-aldehyde in varying degrees as demonstrated by a positive test with 2,4-dinitrophenylhydrazine. Subsequently, the CPG-bound dithymidine 5'-aldehyde was treated with NaBD$_4$ at 25° C. in Tris-HCl buffer (pH 7.0, 30 min.). The resulting CPG-bound [5'-$^2$H]-alcohol was used to synthesize trithymidine $T^{2*}TT$-CPG.

After routine deprotection and purification, the deuterated trimer was compared with an authentic trimer by PAGE (20%, 7M urea) and $^1$H-NMR (D$_2$O). The UV-shadowed images were identical, and the chemical shift patterns were the same, except that for the deuterated trimer the integrated area of peaks δ=4.0–4.2 ppm (corresponding to 5'-methylene hydrogen atoms) was less due to incorporation of deuterium.

Example 2

Synthesis of $C^{3*}TC$

To further demonstrate the site specificity of the isotopic labeling, we prepared a tritiated trimer $C^{3H}TC$ using [$^3$H] NaBH$_4$ as the reducing agent following the same synthetic method described in Example 1. A solution of NaBH$_4$ (3–5 equivalents) in i-PrOH/Tris-HCl (1/1, pH 7.0) was used immediately after the [$^3$H]NaBH$_4$ treatment (0° C., 30 min.) to completely reduce any unreacted aldehyde.

The purified trimer was digested with Snake Venom Phosphodiesterase and Bacterial Alkaline Phosphatase (both from Pharmacia, Piscataway, N.J.). The digested samples were analyzed by reverse-phase HPLC monitored simultaneously by UV and flow-radioactive detectors. All HPLC analyses were done with MILLENNIUM software (Waters, Milford, Mass.) on a Waters 600 Controller with a 996 Photodiode Array UV detector (200–320 nm) (Waters, Milford, Mass.) interfaced with a Packard Radiomatic 545 TR Flow Scintillation Analyzer (0–18.5 Kev, $^3$H flow-counting efficiency at about 40%) (Packard, Meriden, Conn.). Scintillation cocktail (ULTIMA-FLOW AP (Packard, Meriden, Conn.) was auto-mixed with HPLC flow-buffer at a 3:1 ratio after UV detection and pumped into a scintillation flow-cell (500 μl) in about 40 sec delay time. Reverse-phase HPLC was carried out using a NOVA-PAK C$_{18}$ column (3.9×150 nm) (Waters, Milford, Mass.) at 25° C. with isocratic mobile phase (H$_2$O/2M TEAA/CH$_3$CN, 92:5:3, v/v/v, flow rate 0.5 ml/min) over 30 minutes.

The digested samples were repeatedly evaporated with ethylenediamine solution (90% in water) to ensure that all amino hydrogen atoms of the heterocyclic bases were free of $^3$H. Peak index plot was programmed by recording the UV spectra (240–300 nm) at each peak apex (retention time at 3.38 and 7.38 min. respectively) of the chromatogram ($λ_{260}$). The two detected peaks matched those of standard dC and T, respectively. The HPLC profiles revealed that only the thymidine peak carried the $^3$H label.

A control experiment was done in which the trimer CTC was made by standard synthesis in the presence of [$^3$H] NaBH$_4$, but in the absence of redox chemistry. Minimal reactivity was found.

Example 3 d[A$_3$], d[C$_3$], and d[G$_3$] Phosphorothioates and Methyl Phosphonates

Tests similar to those described in Example 2 were conducted on d[A$_3$], d[C$_3$], and d[G$_3$] phosphorothioates and methyl phosphonates, and site-specific labeling without structural modification was observed in each instance.

Example 4

Synthesis of Tritium Labeled Oligonucleotide 25-mer

Figure 3:
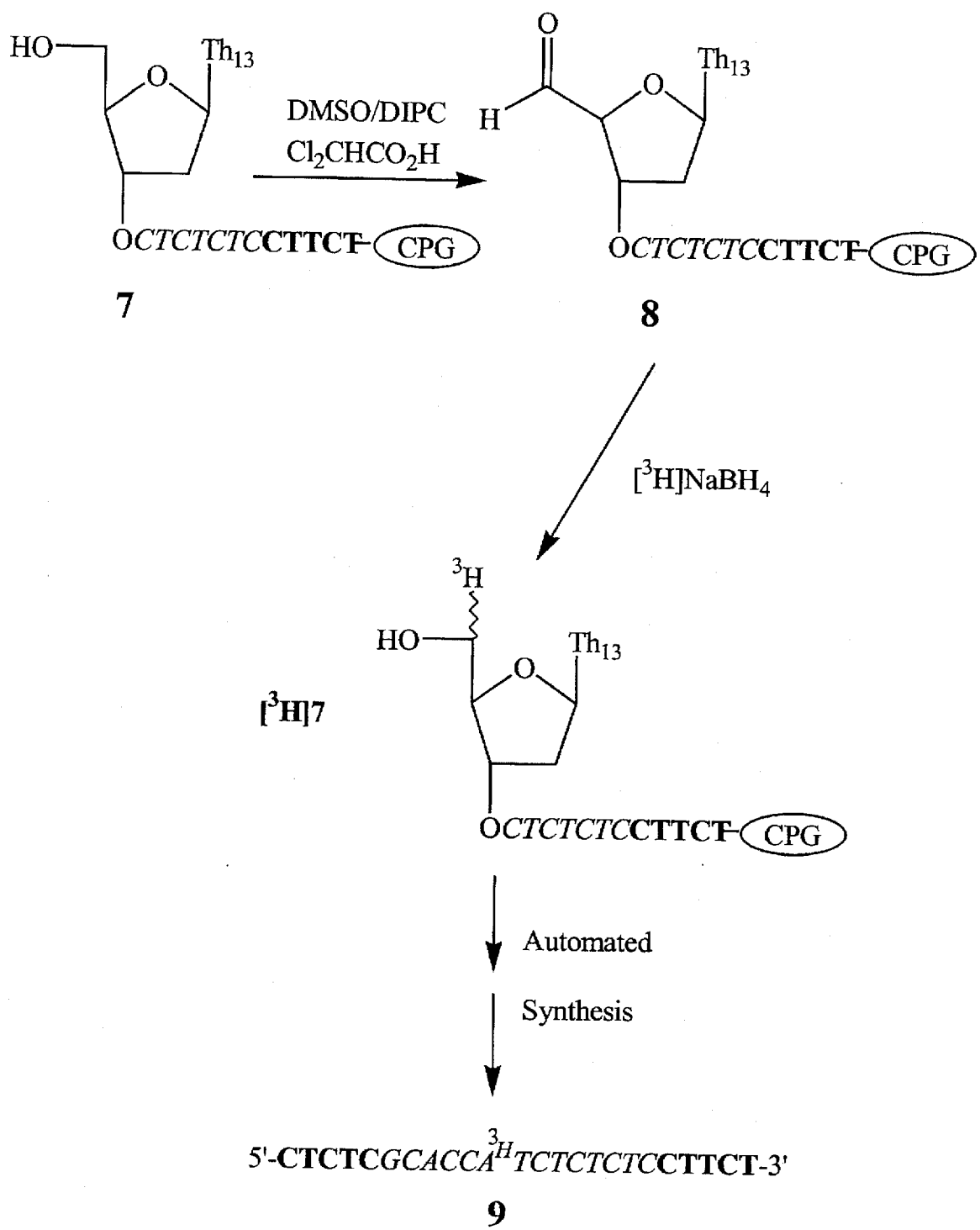
FIG. 3 is a schematic representation of the chemical synthesis and tritium labeling of SEQ ID NO 1. Bold-faced nucleotides have methylphosphonate linkages and italic-faced nucleotides have phosphorothioate linkages.

The trityl-off chimeric oligonucleotide SEQ ID NO 2 (structure 7 in FIG. 3) was auto-synthesized on a 4×1 μmol scale using phosphoramidite chemistry. The vacuum-dried, CPG-bound SEQ ID NO 2 was placed in an eppendorf tube (1.5 ml) and treated with DMSO/DIPC/Cl$_2$CHCO$_2$H (250 μl/50 μl/4 μl) at 25° C. for 2 hours. After washing with CH$_3$CN (10×1 ml) the aldehyde (structure 8 in FIG. 3) was transferred to a glass vial containing a solution of [$^3$H] NaBH$_4$ (25 mCi, 65 mCi/μmol, American Radiolabeled Chemicals, St. Louis, Mo.) in i-PrOH/1M Tris-HCl (200 μl, 95/5) and the reaction was kept at 25° C. for 2 hours. The reaction mixture was cooled to 0° C., a solution of NaBH$_4$ (0.1M in 200 μl of 1M Tris-HCl, pH 7.0) was added. After 15 min., the supernatants were removed and the CPG was sequentially washed with 1M Tris-HCl (pH 7.0, 0.5 ml), 2N CH$_3$CO$_2$H (0.5 ml) and ethanol (2×1 ml). After final wash with CH$_3$CN (10×1 ml), synthesis of the remaining 13-mer was completed. The crude CPG-bound product (structure 9 in FIG. 3) was treated with NH$_4$OH (28%, 3 ml, 25° C., 2 h). Evaporation with a Speed-Vac yielded a dried yellow pellet, which was immediately incubated with a solution of ethylenediamine/ethanol/water (50/45/5, v/v/v, 320 μl) at 25° C. for 4.5 hours. Evaporation gave the crude product (structure 9) as a yellow pellet. PAGE purification (20%, 7M urea) gave the product 9 as a white pellet (AU$_{260}$=69 OD, $λ_{MAX}$=266.7 nm, 354.3 μCi, 1.16 mCi/μmol).

Example 5

Site-specific Labeling of a 25-mer Oligonucleotide

We synthesize a 25-mer anti-HIV antisense oligonucleotide (SEQ ID NO 1) according to the method of the invention. The synthesis of SEQ ID NO (depicted in FIG. 3) was conducted to introduce a tritium label at T$_{13}$, a site quite distant from the 3'-end and the usual starting point for possible exonuclease action. The CPG bound 13-mer alcohol (structure 7 in FIG. 3) was made by automated synthesis in the trityl-off mode. Oxidation yielded the corresponding 13-mer 5'-aldehyde (structure 8 in FIG. 3), which was immediately subject to reduction by [$^3$H]NaBH$_4$ to give the tritium-labeled version of structure 7. A solution of NaBH$_4$ (3–5 equivalents) in i-PrOH/Tris-HCl (1/1, pH 7.0) was used immediately after the [$^3$H]NaBH$_4$ treatment (0° C., 30 min.) to completely reduce any unreacted aldehyde. By automated synthesis, structure 7 was elongated to yield the CPG-bound 25-mer. Deprotection and purification yielded the tritium labeled SEQ ID NO 1 with high radio-specific activity (1.16 mCi/μmol).

Ion-exchange HPLC was done on a GEN-PAK FAX column (4.6×100 mm) (Waters, Milford, Mass.) at 65° C. using a gradient (80% A to 100% B over 50 min.) of Buffer A (25 mM Tris-HCl, pH 8, 10% CH$_3$CN) to Buffer B (2.5 mM Tris HCl, 2M LiCl, pH 8.5, 10% CH$_3$CN), with a flow rate 0.5 ml/min. Tritium labeled SEQ ID NO 1 was co-injected with unlabeled SEQ ID NO 1. PAGE profiles of tritium labeled SEQ ID NO 9 were found to be identical.

b) contacting the aldehyde with [$^3$H]NaBH$_4$ such that the oligonucleotide is labeled with tritium.

2. The method according to claim 1, wherein the oxidizing agent is dimethylsulfoxide.

3. The method according to claim 1, wherein the oxidizing agent is dimethylsulfoxide, a carbodiimide, and an acid having a pK$_a$ of from about 1.0 to 2.5.

4. The method according to claim 3, wherein the acid is phosphoric acid, dichloroacetic acid, or a mixture thereof.

5. The method according to claim 4, wherein the carbodiimide is N,N'-diisopropylcarbodiimide or N,N'-dicyclohexylcarbodiimide.

6. The method according to claim 1, wherein the oxidizing agent is a periodinane.

---

---

We claim:

1. A method of synthesizing tritium labeled oligonucleotides comprising:

a) contacting a nascent oligonucleotide having a 5' hydroxyl group with an oxidizing agent that will oxidize the hydroxyl group to an aldehyde; and 7. The method according to claim 1, wherein the oxidizing agent is the Dess-Martin periodinane.

8. The method according to claim 1, wherein the oxidizing agent is dimethylsulfoxide and acetic anhydride.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:1:

CTCTCGCACC ATCTCTCTCC TTCT        24

( 2 ) INFORMATION FOR SEQ ID NO:2:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: YES ( x i ) SEQUENCE DESCRIPTION: SEQ ID NO:2:

TCTCTCTCCC TTCT        14